United States Patent
Crane

(10) Patent No.: US 6,491,919 B2
(45) Date of Patent: *Dec. 10, 2002

(54) AQUEOUS IMMUNOLOGIC ADJUVANT COMPOSTIONS OF MONOPHOSPHORYL LIPID A

(75) Inventor: R. Thomas Crane, Hamilton, MT (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/338,182

(22) Filed: Jun. 22, 1999

(65) Prior Publication Data

US 2002/0009456 A1 Jan. 24, 2002

Related U.S. Application Data

(63) Continuation-in-part of application No. 09/054,140, filed on Apr. 2, 1998, now abandoned, which is a continuation-in-part of application No. 08/831,073, filed on Apr. 1, 1997, now abandoned.

(51) Int. Cl.$^7$ ............................................. A61K 39/38
(52) U.S. Cl. ................................ 424/184.1; 424/193.1; 514/25; 514/772.4
(58) Field of Search .......................... 424/184.1, 193.1; 514/25, 772.4

(56) References Cited

U.S. PATENT DOCUMENTS

| | | | | |
|---|---|---|---|---|
| 4,436,727 A | * | 3/1984 | Ribi | 424/177 |
| 4,436,728 A | * | 3/1984 | Ribi et al. | 424/177 |
| 4,912,094 A | * | 3/1990 | Myers et al. | 514/54 |
| 5,326,857 A | * | 7/1994 | Yamamoto et al. | 536/23.3 |
| 5,552,141 A | * | 9/1996 | Ribi | 424/184.1 |
| 5,554,372 A | * | 9/1996 | Hunter | 424/280.1 |
| 5,855,913 A | | 1/1999 | Hanes et al. | |
| 5,985,309 A | * | 11/1999 | Edwards et al. | 424/426 |

FOREIGN PATENT DOCUMENTS

| | | |
|---|---|---|
| GB | 2220211 A | 1/1990 |
| WO | WO 94/21292 A1 | 9/1994 |
| WO | WO 98/43670 A2 | 10/1998 |
| WO | WO 99/56776 A2 | 11/1999 |

OTHER PUBLICATIONS

Boeckler, et al. "Immunogenicity of nw Heterobifunctional Cross–Linking Reagents Used in the Conjugation of Synthetic Peptides to Liposomes" *J. of Immunological Methods* vol. 191 (1) May 1996 pp. 1–10.

Sasaki, et al. "Monophoshoryl Lipid A Enhances Both Humoral and cell–mediated Immune Responses to DNA Vaccination Against Human Immunodeficiency Virus Type 1" *Infection and Immunity*, vol. 65 (9) Sep. 1997 pp. 3520–3528.

Verheul, et al. "Beneficial Effects of Additional Adjuvants on the Immune Response to Haptenated Liposomes" *J. of Liposome Research* vol. 6 (2) 1996 pp. 397–414.

* cited by examiner

*Primary Examiner*—James O. Wilson
*Assistant Examiner*—Ganapathy Krishnan
(74) *Attorney, Agent, or Firm*—Townsend and Townsend and Crew LLP

(57) ABSTRACT

An aqueous adjuvant composition comprising an attenuated lipid A derivative and a non-immunostimulatory surfactant or surfactants enhances the immunological response in a warm blooded animal to a protein antigen. Attenuated lipid A derivatives useful according to the subject invention include monophosphoryl lipid A and 3-O-deacylated monophosphoryl lipid A. A surfactant or mixtures of surfactants are dissolved in a solvent. 1,2 Dipalmitoyl-sn-glycero-3-phosphocholine is a preferred surfactant. The dissolved surfactant is added to an attenuated lipid A derivative to obtain a mixture. The molar ratio of attenuated lipid A derivative to surfactant in the mixture is about 4:1. The solvent is evaporated and water is added to the resulting film. The suspension is sonicated in a 60° C. water bath until it becomes clear. Animals administered the adjuvant formulation exhibited increased antibody responses to a given antigen as well as displayed enhanced lymphocyte proliferative and cytotoxic T-lymphocyte responses. Intranasal administration of the aqueous adjuvant composition and an antigen stimulates the production of serum and mucosal secreted IgA.

4 Claims, 2 Drawing Sheets

AQUEOUS IMMUNOLOGIC ADJUVANT COMPOSTIONS OF MONOPHOSPHORYL LIPID A

CROSS-REFERENCE TO A RELATED APPLICATION

This application is a continuation-in-part of application Ser. No. 09/054,140, filed Apr. 2, 1998, now abandoned, which is a continuation-in-part of application Ser. No. 08/831,073, filed Apr. 1, 1997, now abandoned.

BACKGROUND OF THE INVENTION

The compounds monophosphoryl lipid A (MLA) and 3-O-deacylated monophosphoryl lipid A (3D-MLA) are attenuated derivatives of the lipid A component of bacterial lipopolysaccharide (LPS). LPS and lipid A are potent immunostimulants inducing both a humoral antibody response and a cell-mediated immune response in patients administered the compounds. Lipid A and LPS however can also display toxic side-effects such as pyrogenicity and local Shwarzman reactions. MLA and 3D-MLA are lipid A-like molecules that have been modified to attenuate the toxicity of LPS.

Like lipid A, the MLA and 3D-MLA molecules have a sugar backbone onto which long chain fatty acids are attached. The backbone is comprised of two six carbon sugar rings in glycosidic linkage. MLA and 3D-MLA are phosphorylated at the 4 position. Five to eight long chain fatty acids (12–14 carbons) are attached to the sugar backbone making MLA and 3D-MLA very hydrophobic molecules which are not readily water soluble.

The attenuated lipid A derivatives (ALDs) MLA and 3D-MLA are used as immunologic adjuvants in prophylactic vaccines for infectious disease and therapeutic vaccines for the treatment of cancerous tumors and chronic infections. Antigen preparations included in most vaccines are often complicated mixtures of water-soluble proteins making it difficult to formulate the water insoluble adjuvant in a water based vaccine. Therefore, MLA and 3D-MLA must be first mixed with solvents before they are added to the antigen preparation. However, the presence of solvents can further complicate the formulation of the vaccine, and in some cases can reduce the efficiency of its components. Further, solvents can irritate mucosal surfaces or cause inflammation at an injection site. A simple formulation of MLA or 3D-MLA containing no interfering co-solvents would allow maximum benefits to be derived from both the adjuvant and the antigen in a vaccine composition. The instant invention satisfies this need.

SUMMARY OF THE INVENTION

The subject invention involves an aqueous formulation of an attenuated lipid A derivative (ALD) and a surfactant and methods for its preparation and storage. Attenuated lipid A derivatives useful according to the subject invention include monophosphoryl lipid A (MLA) and 3-O-deacylated monophosphoryl lipid A (3D-MLA). Aqueous formulations of MLA (MLA/AF) or 3D-MLA (3D-MLA/AF) eliminate the need for undesirable solvents or a co-solvent system for vaccine preparation. The invention provides a stable aqueous composition of the ALD and a surfactant which when administered to mice with an antigen, enhances the cellular and humoral immune response of the animal to that antigen. Surprisingly, the aqueous formulation of the present invention induces high levels of serum and mucosal secreted IgA in immunized animals when administered intranasally. An embodiment of the claimed aqueous composition comprises a MLA or 3D-MLA to surfactant molar ratio of about 4:1 and has a particle size of approximately 50–70 nm. 1,2-Dipalmitoyl-sn-glycero-3-phosphocholine (DPPC) is a preferred surfactant. Unexpectedly, when glycerol is added to the subject aqueous formulation before lyophilization, the composition is restored upon reconstitution with no additional sonication. Successful storage of the subject composition in a lyophilized state allows for convenient storage and transport of the aqueous formulation or vaccine compositions comprising the formulation.

A method of preparing the aqueous composition is disclosed. In one embodiment the ALD and the surfactant are dissolved and uniformly admixed in ethanol. The ethanol is then evaporated leaving a film. Water is added to the film. The ALD and surfactant are suspended in the water by sonication. The suspension is sonicated until clear. Animals administered the claimed composition with an antigen display enhanced humoral and cellular immune responses to that antigen. Methods for using the composition to enhance these responses are also disclosed and claimed.

BRIEF DESCRIPTION OF THE FIGURES

FIG. 1a shows the total IgG antibody titers of mice administered the tetanus toxoid antigen. FIG. 1b shows the IgG2a antibody titers of mice administered the tetanus toxoid antigen. FIG. 1c shows the IgG2b antibody titers of mice administered the tetanus toxoid antigen and FIG. 1d shows the IgG1 antibody titers for the animals.

DETAILED DESCRIPTION OF THE INVENTION

Figure 1:
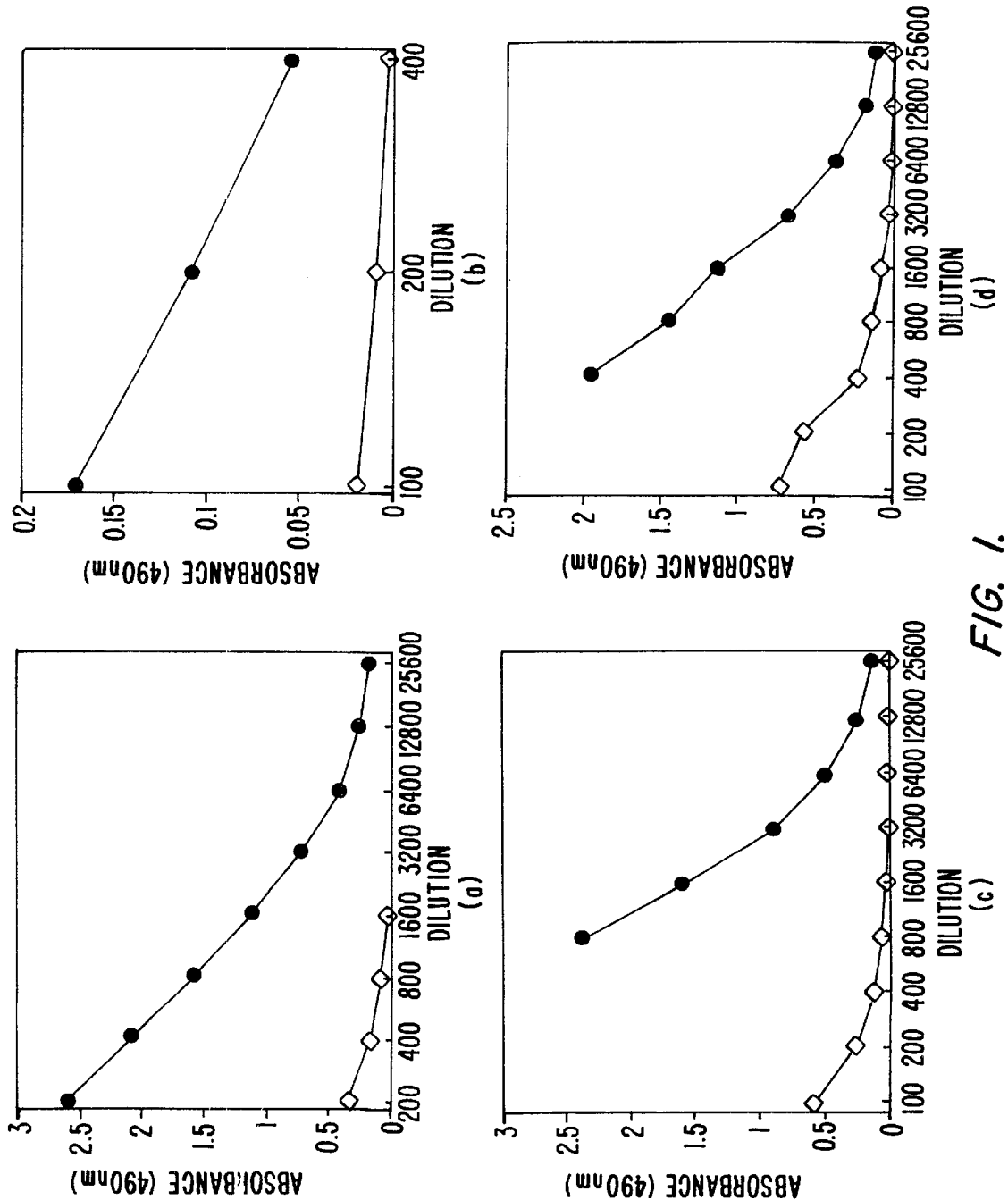
FIGS. 1a–d show the antibody titers of mice administered tetanus toxoid (TT) antigen in 3-O-deacylated monophosphoryl lipid A-aqueous formula (3D-MLA/AF)★ or tetanus toxoid antigen in saline ◊.

The subject invention involves an aqueous adjuvant formulation of an attenuated lipid A derivative (ALD). The ALD and a surfactant are suspended in water in a molar ratio of approximately 4:1 and sonicated to yield a suspension having a particle size of approximately 50–70 nm.

In accordance with the present invention, an attenuated lipid A derivative can be formulated into an aqueous composition to provide a potent adjuvant. An attenuated lipid A derivative is a lipid A-like compound which displays the advantageous immunostimulatory properties of lipid A yet exhibits less of the adverse side affects of that compound. For example, monophosphoryl lipid A (MLA) and 3-O-deacylated monophosphoryl lipid A (3D-MLA) are ALDs that are potent immunostimulants but are surprisingly less toxic than lipid A. Both MLA and 3D-MLA can be used in the compositions of the subject invention and are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 4,912,094 to Myers, et al., also assigned to Ribi ImmunoChem Research, Inc., embodies 3-O-deacylated monophosphoryl lipid A and a method for its manufacture. Disclosures of each of these patents with respect to MLA and 3D-MLA are incorporated herein by reference.

Without going into the details of the prior incorporated by reference patents, monophosphoryl lipid A (MLA) as used herein is derived from lipid A, a component of enterobacterial lipopolysaccharides (LPS), a potent but highly toxic immune system modulator. Edgar Ribi and his associates achieved the production of monophosphoryl lipid A (MLA) referred to originally as refined detoxified endotoxin. MLA is produced by refluxing an endotoxin extract (LPS or lipid A) obtained from heptoseless mutants of gram-negative bacteria in mineral acid solutions of moderate strength (e.g. 0.1 N HCl) for a period of approximately 30 minutes. This treatment results in the loss of the phosphate moiety at position 1 of the reducing end glucosamine.

Coincidentally, the core carbohydrate is removed from the 6 position of the non-reducing glucosamine during this treatment. The resulting product (MLA) exhibits considerably attenuated levels of the endotoxic activities normally associated with the endotoxin starting material, such as pyrogenicity, local Shwarzman reactivity, and toxicity as evaluated in the chick embryo 50% lethal dose assay ($CELD_{50}$). However, it unexpectedly retains the functionality of lipid A and LPS as an immunomodulator.

Another attenuated lipid A derivative which may be utilized in the practice of the present invention is referred to as 3-O-deacylated monophosphoryl lipid A (3D-MLA). 3D-MLA is known as set forth in U.S. Pat. No. 4,912,094, reexamination certificate B1 4,912,094 (the '094 patent), and differs from MLA in that there is selectively removed from the MLA molecule the β-hydroxymyristic acyl residue that is ester linked to the reducing-end glucosamine at position 3 under conditions that do not adversely affect the other groups. 3-O-deacylated monophosphoryl lipid A is available from Ribi ImmunoChem Research, Inc., Hamilton, Mont. 59840.

The MLA and 3D-MLA molecules are a composite or mixture of a number of fatty acid substitution patterns, i.e., heptaacyl, hexaacyl, pentaacyl, etc., with varying fatty acid chain lengths. Thus, these various forms of MLA and 3D-MLA are encompassed by this invention. Further, mixtures of forms of a compound as well as individual compounds produced by synthetic or semisynthetic means are encompassed by this invention. The lipid A backbone that is illustrated in the—094 patent corresponds to the product that is obtained by 3-deacylation of heptaacyl lipid A from *S. Minnesota* R 595. Other fatty acid substitution patterns are encompassed by this disclosure; the essential feature is that the material be 3-O-deacylated.

The modified 3D-MLA utilized in the present invention is prepared by subjecting MLA to alkaline hydrolysis under conditions that result in the loss of but a single fatty acid from position 3 of the lipid A backbone. β-hydroxymyristic fatty acid at position 3 is unusually labile in alkaline media. It requires only very mild alkaline treatment to completely 3-deacylate lipid A. The other ester linkages in lipid A require somewhat stronger conditions before hydrolysis will occur so that it is possible to selectively deacylate these materials at position 3 without significantly affecting the rest of the molecule. The reason for the unusual sensitivity to alkaline media of the ester-linked β-hydroxymyristic fatty acid at position 3 is not known at this time.

Although alkaline hydrolysis procedures are known, it is important to choose conditions that do not cause further hydrolysis beyond the ester linkage to the β-hydroxymyristic at position 3. In general the hydrolysis can be carried out in aqueous or organic media. In the latter case, solvents include methanol (alcohols), dimethyl sulfoxide (DMSO), dimethylformamide (DMF), chloroform, dichloromethane, and the like, as well as mixtures thereof. Combinations of water and one or more of the mentioned organic solvents also can be employed.

The alkaline base can be chosen from among various hydroxides, carbonates, phosphates and amines. Illustrative bases include the inorganic bases such as sodium hydroxide, potassium hydroxide, sodium carbonate, potassium carbonate, sodium bicarbonate, potassium bicarbonate, and the like, and organic bases such as alkyl amines, and include, but are not limited to, diethylamine, triethylamine, and the like.

In aqueous media the pH is typically between approximately 10 and 14 with a pH of about 12 to about 13.5 being the preferred range. The hydrolysis reaction is typically carried out at a temperature of from about 20° C. to about 80° C., preferably about 50° C. to 60° C. for a period of about 10 to about 30 minutes. For example, the hydrolysis can be conducted in 3% triethylamine in water at room temperature (22°–25° C.) for a period of 48 hours. The only requirement in the choice of temperature and time of hydrolysis is that deacylation occurs to remove only the β-hydoxymyristic at position 3.

In practice it has been found that a particularly desirable hydrolysis method involves dissolving lipid A or monophosphoryl lipid A in chloroform:methanol 2:1 (v/v), saturating this solution with an aqueous buffer consisting of 0.5 M $Na_2CO_3$ at pH 10.5, and then flash evaporating the solvent at 45°–50° C. under a vacuum or an aspirator (approximately 100 mm Hg). The resulting material is selectively deacylated at position 3. This process can also be carried out with any of the inorganic bases listed above. The addition of a phase transfer catalyst, such as tetrabutyl ammonium bromide, to the organic solution prior to saturation with the aqueous buffer may be desirable in some cases.

In preparing the composition of the subject invention, generally, the attenuated lipid A derivative (ALD) is combined with the surfactant each being dissolved in a solvent. The solvent is evaporated leaving a film. Water is added to the film and the resulting suspension is sonicated while heated until clear. The final suspension has a particle size of approximately 40–150 nm and preferably from about 50 to about 70 nm.

The ALD and surfactant are combined at a molar ratio of about 10 parts ALD to from about 1 part to about 5 parts surfactant. Preferably, the components are combined in a molar ratio of about 4 parts ALD to 1 part surfactant. Surfactants contemplated for use in the compositions of the subject invention are non-immunostimulatory or non-reactive displaying little or no independent biological activity. As used herein, the terms non-immunostimulatory and non-reactive means the surfactants show little or no appreciable biological activity above non-immune controls. Non-immunostimulatory surfactants useful according to the subject invention include but are not limited to bile salts, natural phospholipids and sphingolipids. Bile salts such as glycodeoxycholate and deoxycholate are useful as surfactants in the claimed compositions. Other suitable surfactants include sphingolipids such as sphingomyelin and sphingosine and phospholipids such as egg phosphatidylcholine, 1,2-Dimyristoyl-sn-glycero-3-phosphoethanolamine, L-α-Phosphatidylethanolamine, and 1,2-Dipalmitoyl-sn-glycero-3-phosphocholine or mixtures thereof. In a preferred embodiment, the phospholipid 1,2-Dipalmitoyl-sn-glycero-3-phosphocholine (DPPC) is the surfactant.

DPPC is accepted for use in humans and is especially effective when the formulation is administered intranasally.

The ALD and surfactant are dissolved and thoroughly admixed in a solvent. Aqueous or organic solvents useful according to the subject invention include chloroform, alcohols (eg. ethanol), dimethyl sulfoxide (DMSO), dimethylformamide (DMF), and the like, as well as mixtures thereof.

The solvent is evaporated from the mixture of ALD and surfactant leaving a film. Water is added to the film and the resulting suspension is sonicated while heated until clear. It is preferred that the suspension be sonicated in a water bath sonicator. The water bath temperature can be from 40° C. to 80° C. and preferably about 60° C. The suspension can be sonicated for periods of 5 minutes to approximately one hour until clear. Periods of sonication will vary depending upon the volume and concentration of the suspension but can be readily determined by one skilled in the art. The final suspension has a particle size of approximately 40–150 nm and preferably from about 50 to about 70 nm.

The aqueous formulation of the subject invention can be lyophilized for shipment and storage. When the composition is lyophilized in the presence of glycerol, unexpectedly, it can be reconstituted without additional sonication. Glycerol present in the composition at about 2 percent to about 40 percent, and preferably about 2 to about 10 percent volume to volume, allows the lyophilized composition to be restored upon the addition of water. The ability to reconstitute the aqueous formulation to its original particle size by simply adding water is a distinct advantage for vaccination in the field away from laboratory equipment. Further advantages to being able to ship the subject composition in a lyophilized form include reduced load weights, no requirement for refrigeration and increased stability. ALDs present in the compositions of the subject invention are believed to be protected from hydrolysis in this lyophilized state. Additionally, the concentration of ALD presented to the vaccinee can be varied by adjusting the volume for reconstitution. For example, ten milliliters of a composition containing 1 mg/ml of ALD can be lyophilized and reconstituted with 1 ml of water to yield aqueous compositions of 10 mg/ml ALD. Glycerol also stabilizes protein antigens present in vaccine compositions of the subject invention during lyophilization. Other components which could be used to stabilize the subject composition for lyophilization include but are not limited to polypropylene glycol, polyethylene glycol or other poly alcohols appropriate for parenteral use.

An effective amount of the composition of the subject invention is administered to a warm-blooded animal with an antigen to enhance the immune response of the animal to that antigen. The composition of the subject invention enhances both the humoral immune response of an animal to an antigen as well as the cellular immune response. The amount of antigen administered to elicit the desired response can be readily determined by one skilled in the art and will vary with the type of antigen administered, route of administration and immunization schedules. For example, 0.1 μg of tetanus toxoid administered with the claimed composition subcutaneously to a mouse in two immunizations 21 days apart elicits a humoral immune response to that antigen. Administered intranasally, the composition of the subject invention and an antigen stimulate the production of cytotoxic T-lymphocytes. Hepatitis B surface antigen (2.5 μg) administered intranasally at days 0 and 21 in the claimed composition stimulated the production of cytotoxic T-lymphocytes in immunized animals. Further, the composition of the subject invention is particularly effective in eliciting an IgA response in immunized animals when administered intranasally. Mice administered 0.5–12.5 μg of tetanus toxoid in an aqueous formulation of 3-O-deacylated monophosphoryl lipid A (3D-MLA/AF) displayed increased IgA titers to that antigen. An effective amount of the composition of the subject invention is that amount which stimulates or enhances an immune response. For example, an effective amount of the claimed composition can contain from 1 to about 250 micrograms of attenuated lipid A derivative and preferably from about 25 to about 50 micrograms based upon administration to a typical 70 kg adult patient.

The following examples are offered to further illustrate but not limit both the compositions and the method of the present invention. It is to be understood that the mouse models presented herein are representative of warm blooded animals and correlate reasonably with events for other warm blooded animals, including humans. All percentages are by weight and all solvent mixture proportions are by volume unless otherwise noted.

EXAMPLE 1

Preparation of an Aqueous Formulation of an Attenuated Lipid A Derivative

An aqueous preparation of 3-O-deacylated monophosphoryl lipid A (3D-MLA/AF) according to the subject invention comprising 1000 μg/ml 3D-MLA (Ribi ImmunoChem Research, Inc., Hamilton, Mont. 59840), an attenuated form of lipid A from Salmonella minnesota R 595 and 118 μg/ml 1,2 Dipalmitoyl-sn-glycero-3-phosphocholine (DPPC) in Water for Injection was prepared as follows:

A solution of DPPC was prepared at a concentration of 4 mg/ml in ethanol and vortexed until clear. A 2.7 ml aliquot of the DPPC solution was added to a vial containing 100 mg lyophilized 3D-MLA and swirled gently to wet the 3D-MLA. The ethanol was removed by blowing a stream of filtered nitrogen gently into the vial. Water for Injection (91.7 ml) was added to the vial which was then stoppered, sealed and suspended in a Labline 9303 water bath sonicator. The suspension was sonicated for 10 minutes at 60° C. until clear. The resulting aqueous formulation contained particles of 70 nm measured by a PSC100 Spectrometer from Malvern Instruments and was filter sterilized through a 0.2 μm filter.

EXAMPLE 2

Lyophilization and Reconstitution of the Aqueous Formulation

Two percent glycerol was added to an aqueous formulation of MLA prepared as in Example 1. The mixture was aliquoted in vials at volumes from one to 10 ml. Vials were frozen in a lyophilizer at a shelf temperature of −45° C. After 2 hr, the condenser and vacuum were engaged and the shelf temperature was set at −10° C. The shelf temperature was changed to +10° C. after 48 hr and held at the new temperature for 24 hr. The shelf temperature was then set to +25° C. for a final 24 hr. Following lyophilization, vials were reconstituted with 1 ml of Water for Injection (WFI). Reconstitution was performed by swirling the water in the vials. All vials were clear with no visible precipitate. Portions of the concentrated formulations were diluted in WFI to yield a final solution of 1 mg/ml prior to particle size determination.

TABLE 1

| Vialed Amount (ml) | Formulation Conc. Following Reconstitution | Particle Size (nm) |
|---|---|---|
|  | prior to lyophilization | 83.5 |
| 1 ml | 1 mg/ml MLA | 71.9 |
| 2 ml | 2 mg/ml MLA | 71.1 |
| 3 ml | 3 mg/ml MLA | 71.0 |
| 4 ml | 4 mg/ml MLA | 71.4 |
| 5 ml | 5 mg/ml MLA | 75.9 |
| 6 ml | 6 mg/ml MLA | 79.4 |
| 7 ml | 7 mg/ml MLA | 70.4 |
| 8 ml | 8 mg/ml MLA | 74.4 |
| 9 ml | 9 mg/ml MLA | 74.6 |
| 10 ml | 10 mg/ml MLA | 80.7 |

Table 1 shows that the aqueous formulation of the subject invention is restored to its original particle size after lyophilization by the addition of water.

EXAMPLE 3
Stimulation of an Antibody Response

Mice immunized with tetanus toxoid (TT) in the aqueous formulation of the subject invention generated tetanus toxoid specific antibody. The TT-specific total IgG titer and IgG isotypes (2a, 2b, 1) titers were measured by enzyme-linked immunosorbent assay (ELISA) in the sera of mice following immunization.

Female ICR mice were immunized with a dose of vaccine containing 0.1 µg of tetanus toxoid (TT) +50 µg 3D-MLA/AF or 0.1 µg TT in saline. 3D-MLA/AF was prepared as in Example 1. The vaccines were administered by subcutaneous injection on days 0 and 21. Serum was collected 14 days post secondary immunization and assayed by standard ELISA techniques to report the relative amounts of tetanus-toxoid specific antibody of $IgG_1$, $IgG_{2a}$ and $IgG_{2b}$ isotypes as well as total IgG.

FIG. 1 shows the tetanus toxoid specific antibody titer generated by 3D-MLA/AF. 3D-MLA/AF when administered with the tetanus toxoid antigen stimulates the production of IgG antibody in immunized animals and in particular actively stimulates $IgG_{2a}$ production.

EXAMPLE 4
Stimulation of Cellular Proliferation

Mice primed by immunization with the adjuvant composition of the subject invention and a purified protein derivative (PPD) (tuberculin) exhibited a proliferative response in vitro when spleen cells were treated with that antigen.

Figure 2:
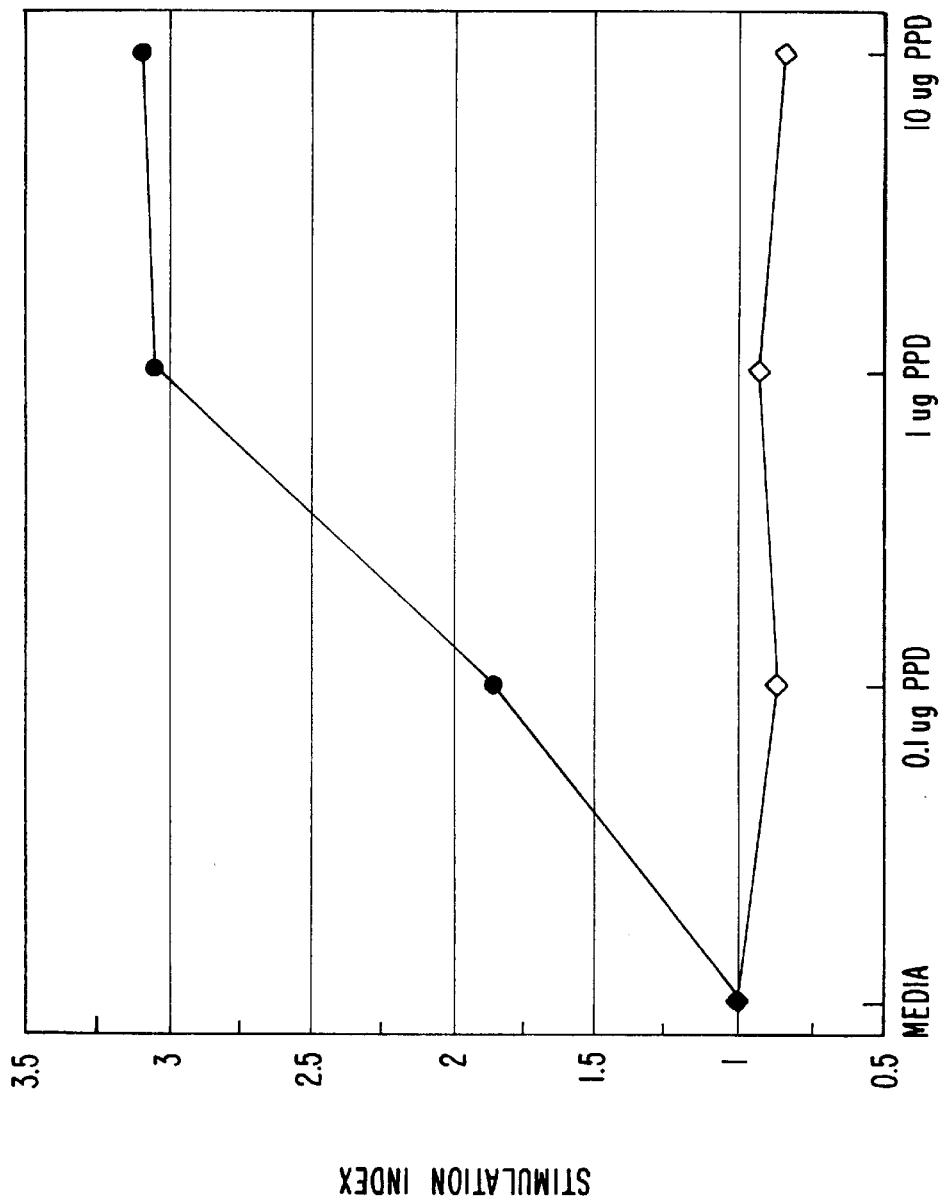
FIG. 2 shows the T-cell proliferative response in mice immunized with a purified protein derivative. The proliferative response in mice administered tetanus toxoid in 3D-MLA/AF ★ and normal controls ◊ are shown 14 days post primary vaccination.

Female BALB/c mice were immunized by subcutaneous injection with a dose of vaccines containing 50 µg PPD+50 µg 3D-MLA/AF. 3D-MLA/AF was prepared as in Example 1. Spleen cells were harvested 14 days after immunization and used as a source of lymphocytes in a proliferation assay. The spleen cells were cultured for 96 hr in microtiter wells at a concentration of $10^6$ cells/ml in media containing 0.1, 1 or 10 µg PPD/ml. Tritiated thymidine was added to the cultures during the final 24 hr of incubation. The cells were harvested on glass fiber filters and tritium incorporation was determined. Stimulation indices were determined by dividing counts per minute (CPM) of cells stimulated with PPD by the CPM of cells cultured in media alone. The resulting data are shown in FIG. 2.

EXAMPLE 5
Stimulation of a Cytotoxic T-lymphocyte Response

The induction of a cytotoxic T-lymphocyte response after administration of the aqueous adjuvant composition of the subject invention and a protein antigen was detected by a cytotoxicity assay. Groups of C57/BL/6 mice were given a primary immunization subcutaneously (inguinal region) with 25 µg ovalbumin (OVA) formulated in 3D-MLA/AF. 3D-MLA/AF was prepared as in Example 1. The injected volume was 200 µl. Twenty-one days later three mice per experimental group were killed and spleens removed and pooled as single cell suspensions and counted.

Spleen cells ($75\times10^6$ cells in 3–4 ml media) from the experimental groups were placed in a 25 $cm^2$ T-flask. Next, 1.0 ml of irradiated (20,000 rads) E.G7 (OVA) cells at $5\times10^6$/ml were added to the flask. The volume was brought to 10 ml. The cultures were maintained by placing the T-flasks upright in a 37° C., 5% $CO_2$ incubator for four days. On day 4 the surviving cells were recovered from the flasks, washed 1×, resuspended in 5.0 ml, and counted.

Recovered effector cells were adjusted to $5\times10^6$ viable cells/ml and 100 µl volumes were diluted serially in triplicate in wells of 96 well round-bottom plates (Corning 25850) using 100 µl/well of media as a diluent. Next, 100 µl volumes of $^{51}Cr$-labelled (see below) targets [E.G7 (OVA)-an ovalbumin gene transfected EL-4 cell line] at $1\times10^5$ cells/ml were added to the wells. Spontaneous release (SR) wells contained 100 µl of targets and 100 µl of media. Maximal release (MR) wells contained 100 µl of targets and 100 µl detergent (2% Tween 20). Effector/target (E/T) ratios were 50:1, 25:1, 12.5:1, 6.25:1. The plates were centrifuged at 400×g and incubated at 37° C., 5% $CO_2$ for 4 hr. After the incubation the well supernatants were collected using a Skatron Supernatant Collection System.

$$\text{Percent specific lysis} = 100 \times \left[\frac{(\text{Exp. Release} - SR)}{(MR - SR)}\right]$$

Target cells, E.G7 (OVA), were labelled with $^{51}Cr$ (sodium chromate) as follows. In a total volume of 1.0 ml were mixed $5\times10^6$ target cells and 250 µCi $^{51}Cr$ in 15 ml conical tube. The cell suspensions was incubated in a 37° C. water bath for 90 min., with gentle mixing every 15 min. After incubation the labelled cells were washed 3× by centrifugation and decanting with 15 ml volumes of media. After the third centrifugation the cells were resuspended in 10 ml of fresh media and allowed to stand at room temperature for 30 min. and then centrifuged. The cells were finally resuspended in media to $1\times10^5$ cells/ml. The results of the cytotoxicity assay are presented in Table 2.

TABLE 2

| | % Cytotoxicity ($^{51}Cr$-release) Effector:Target Ratio | | | |
|---|---|---|---|---|
| Material | 50:1 | 25:1 | 12.5:1 | 6.25:1 |
| PBS* | 13 | 10 | 7 | 2 |
| 3D-MLA/AF | 61 | 60 | 59 | 45 |
| Non-immune spleen cells | 8 | 4 | 2 | 2 |

*phosphate buffered saline

EXAMPLE 6
Stimulation of an Antibody Response by Intranasal Administration of the Aqueous ALD formulation Mice administered tetanus-toxoid (TT) in 3D-MLA/AF intranasally produced IgA titers detectable in both serum and fecal extracts. Further, intranasal administration of the aqueous formulation of the subject invention and TT produced high titers of the IgG isotypes $IgG_{2a}$ and $IgG_{2b}$.

Groups of ICR mice were given intranasally, 0.5, 2.5, 10 or 12.5 µg tetanus toxoid in phosphate buffered saline (PBS)

or admixed with 25 μg 3D-MLA/AF. 3D-MLA/AF was prepared as in Example 1. Mice were primed on day 0, bled on day 10 (d10P1°), boosted on day 14, bled on day 24 (d10P2°), boosted on day 28, bled on day 38 (d10P3°). ELISA for IgG- and IgA specific anti-tetanus toxoid antibody was done on pooled sera from each bleed. Fecal extracts were examined on day 22 (d7P2°). IgG and IgA titers of sera and fecal extracts of immunized mice are shown in Tables 3–6.

EXAMPLE 7

Stimulation of an Immune Response to Hepatitis B Surface Antigen by Intranasal Administration of the Aqueous ALD Formulation Mice administered hepatitis B surface antigen (HBSAG) in the composition of the subject invention intranasally produced serum IgG and IgA titers to that antigen. Secretory IgA was detected in vaginal washes and the induction of a

TABLE 3

| | | Serum Anti-Tetanus Toxoid Titer$^{-1}$ | | | | | |
|---|---|---|---|---|---|---|---|
| | | IgG-Specific | | | IgA-Specific | | |
| Vaccine* | Route | d10P1° | d10P2° | d10P3° | d10P1° | d10P2° | d10P3° |
| 0.5 μg TT + PBS | IN | 200 | 400 | 25,600 | <200 | <200 | <200 |
| 2.5 μg TT + PBS | IN | 400 | 51,200 | 25,600 | <200 | <200 | <200 |
| 12.5 μg TT + PBS | IN | 3,200 | 51,200 | 102,400 | <200 | 200 | 400 |
| 0.5 μg TT + 3D-MLA/AF | IN | 12,800 | >409,600 | >409,600 | <200 | 800 | 6,400 |
| 2.5 μg TT + 3D-MLA/AF | IN | 51,200 | >409,600 | >409,600 | <200 | 12,800 | 25,600 |
| 12.5 μg TT + 3D-MLA/AF | IN | 102,400 | >409,600 | >409,600 | <200 | 25,600 | 102,400 |
| 0.5 μg TT + PBS | SQ | 800 | 204,800 | 409,600 | <200 | <200 | <200 |

*n = 4

TABLE 4

IgG Isotype Analysis of Serum from d10P3° Bleeds in Table 3.

| | | Anti-Tetanus Toxoid Titer$^{-1}$ | | |
|---|---|---|---|---|
| Vaccine | Route | IgG$_1$ | IgG$_{2a}$ | IgG$_{2b}$ |
| 0.5 μg TT + PBS | IN | 25,600 | 6,400 | 25,600 |
| 2.5 μg TT + PBS | IN | 51,200 | 3,200 | 25,600 |
| 12.5 μg TT + PBS | IN | 204,800 | 12,800 | 51,200 |
| 0.5 μg TT + 3D-MLA/AF | IN | 819,200 | 409,600 | 819,200 |
| 2.5 μg TT + 3D-MLA/AF | IN | >819,200 | 819,200 | >819,200 |
| 12.5 μg TT + 3D-MLA/AF | IN | >819,200 | >819,200 | >819,200 |
| 0.5 μg TT + PBS | SQ | 819,200 | 6,400 | 25,600 |
| Normal Mouse Sera | — | <400 | <400 | <400 | cytotoxic T-lymphocyte response was detected by a cytotoxicity assay.

Groups of Balb/C mice were given a primary immunization (1°) intranasally with 2.5 μg HBsAg+10 μg 3D-MLA/AF in a volume of 20 μl. 3D-MLA/AF was prepared as in Example 1. Twenty-one days later mice were given a secondary immunization (2°) of 7.5 μg HBsAg+10 μg 3D-MLA/AF intranasally in 20 μl. A tertiary immunization (3°) identical in composition to the secondary immunization was administered 28 days after the secondary immunization. Assays were conducted to detect cytotoxic T-lymphocyte activity at 16 days post secondary immunization (d16,post 2°) and 8 days post tertiary immunization (d8, post 3°). Serum and mucosal antibody titers were assessed at 22 days post secondary immunization (d22, post 2°) and 21 days post

TABLE 5

| | | Serum Anti-Tetanus Toxoid Titer$^{-1}$ | | | | Fecal Extract d7P2° | |
|---|---|---|---|---|---|---|---|
| | | IgG-Specific | | IgA-Specific | | | |
| Vaccine | Route | d10P2° | d10P3° | d10P2° | d10P3° | IgG | IgA |
| TT* + 3D-MLA/AF/PBS | IN | >102,400 | >>102,400 | 6,400 | 25,600 | <50 | 1,600 |
| TT + DPPC/PBS | IN | 6,400 | 6,400 | 100 | 200 | <50 | <50 |
| TT + 3D-MLA/AF/PBS | SQ | >102,400 | >102,400 | 100 | 100 | <50 | <50 |
| Normal Mouse Sera | — | 50 | 50 | 100 | 100 | <50 | <50 |

*10 μg of tetanus toxoid were administered

TABLE 6

IgG Isotype Analysis of Serum from d10P3° Bleeds in Table 5.

| | | Anti-Tetanus Toxoid Titers$^{-1}$ | | |
|---|---|---|---|---|
| Vaccine | Route | IgG$_1$ | IgG$_{2a}$ | IgG$_{2b}$ |
| TT + 3D-MLA/AF/PBS | IN | >819,200 | 102,400 | 409,600 |
| TT + DPPC/PBS | IN | 25,600 | 1,600 | 3,200 |
| TT + 3D-MLA/AF/PBS | SQ | >819,200 | 51,200 | 102,400 |
| Normal Mouse Sera | — | <400 | <400 | <400 | tertiary immunization (d21, post 3°). All assays were conducted by methods standard in the art and described in previous Examples 3 and 5. Results from this experiment are shown in Tables 7–9.

TABLE 7

| | | % Cytotoxicity ($^{51}$Cr-release) | | | |
|---|---|---|---|---|---|
| | | Effector:Target Ratio | | | |
| Material | Day | 50:1 | 25:1 | 12.5:1 | 6.25:1 |
| 3D-MLA/AF | d16, post 2° | 38 | 22 | 15 | 9 |
| Vehicle | | 3 | 2 | 0 | 0 |

TABLE 7-continued

| | | % Cytotoxicity ($^{51}$Cr-release) Effector:Target Ratio | | | |
|---|---|---|---|---|---|
| Material | Day | 50:1 | 25:1 | 12.5:1 | 6.25:1 |
| Non-immune spleen cells | | 3 | 3 | 0 | 0 |
| 3D-MLA/AF | d8, post 3° | 82 | 65 | 49 | 36 |
| Vehicle | | 5 | 2 | 1 | 1 |
| Non-immune spleen cells | | 7 | 5 | 3 | 3 |

TABLE 8

| | | Anti HBsAg Titer$^{-1}$ | | |
|---|---|---|---|---|
| Material | Day | IgG$_1$ | IgG$_{2a}$ | IgA |
| 3D-MLA/AF | d22, post 2° | 256,000 | 64,000 | 1,600 |
| Vehicle | | <2,000 | <2,000 | <200 |
| 3D-MLA/AF | d21, post 3° | 1,000,000 | 1,000,000 | 25,600 |
| Vehicle | | <2,000 | <2,000 | <200 |

Groups of Balb/C mice were immunized with 2.5 µg HBsAg+10 µg 3D-MLA/AF intranasally and boosted intranasally with 7.5 µg HBsAg+10 µg 3D-MLA/AF 21 days later. Vaginal samples were collected 10 days after the booster immunization.

TABLE 9

| | Vaginal Wash Anti-HBSAG Titer$^{-1}$ | |
|---|---|---|
| Material | IgG | IgA |
| 3D-MLA/AF | 100 | 6400 |
| Vehicle | <50 | <50 |

The intranasal administration of HBsAg in the composition of the subject invention stimulated both a humoral and cellular immune response to that antigen. Intranasal immunization with the antigen formulated in 3D-MLA/AF induced a cytotoxic T-lymphocyte response and antigen specific humoral and mucosal immune responses.

EXAMPLE 8
Generation of a Protective Immune Response to Influenza by Intranasal Administration of the Aqueous ALD Formulation Mice immunized intranasally with FLUSHIELD influenza vaccine containing hemagglutinin antigen formulated in the composition of the subject invention produced both IgG and IgA which were recovered in vaginal washes. Immunized mice were also protected 100% from subsequent influenza challenge.

ICR mice were immunized three times at 21 day intervals intranasally with FLUSHIELD influenza vaccine (Wyeth-Lederle) containing 0.3 µg hemagglutinin antigen (HA)+10 µg 3D-MLA/AF. 3D-MLA/AF was prepared as in Example 1. Vaginal washes were collected 14 days after the final immunization. Mice were challenged with 10 LD$_{50}$ (lethal dose 50) of infectious influenza A/HK/68 thirty-five days after the final immunization and monitored for mortality.

TABLE 10

| Group | IgA Vaginal Wash | IgG Vaginal Wash | % Protection |
|---|---|---|---|
| Nonimmune | <20 | <20 | 0 |
| Vehicle | 160 | 80 | 60 |
| 3D-MLA/AF | 2560 | 1280 | 100 |

EXAMPLE 9
Compositions of Monophosphoryl Lipid A

Monophosphoryl lipid A (MLA) can be formulated into the aqueous compositions of the subject invention and administered in the same quantities and amounts as in Examples 1–7 to produce similar results.

It is understood that the foregoing examples are merely illustrative of the present invention. Certain modifications of the compositions and/or methods employed may be made and still achieve the objectives of the inventions. Such modifications are contemplated as within the scope of the claimed invention.

What is claimed is:

1. A dry formulation of an immunostimulatory adjuvant, said formulation comprising:

(a) an immunostimulatory adjuvant which is a member selected from monophosphoryl lipid A, 3-O-deacylated monophosphoryl lipid A and combinations thereof;

(b) a non-immunostimulatory surfactant; and (c) glycerol in an amount sufficient to provide a clear suspension of particles of said immunostimulatory adjuvant upon contacting said formulation with water without sonication.

2. The formulation according to claim 1, wherein said particles are from about 40 nm to about 150 nm in size.

3. The formulation according to claim 2, wherein said particles are from about 50 nm to about 70 nm in size.

4. The formulation according to claim 1, wherein said non-immunostimulatory surfactant is 1,2-dipalmitoyl-sn-glycero-3-phosphocholine.

* * * * *